United States Patent [19]

Herron

[11] 4,061,630
[45] Dec. 6, 1977

[54] 7-SUBSTITUTED-UREIDO-3-CARBAMOYLOXYMETHYL CEPHALOSPORIN ANTIBIOTICS

[75] Inventor: David K. Herron, Indianapolis, Ind.

[73] Assignee: Eli Lilly and Company, Indianapolis, Ind.

[21] Appl. No.: 660,197

[22] Filed: Feb. 20, 1976

[51] Int. Cl.² .................. A61K 31/545; C07D 501/20; C07D 501/32; C07D 501/34
[52] U.S. Cl. ...................................... 544/16; 424/246; 544/22
[58] Field of Search ................................... 260/243 C

[56] References Cited

U.S. PATENT DOCUMENTS

| | | | |
|---|---|---|---|
| 3,673,183 | 6/1972 | Erickson | 260/243 C |
| 3,687,949 | 8/1972 | Holdrege | 260/243 C |
| 3,706,746 | 12/1972 | Bosshardt et al. | 260/243 C |
| 3,741,962 | 6/1973 | Breuer | 260/243 C |
| 3,956,292 | 5/1976 | Cooper | 260/243 C |
| 3,966,709 | 6/1976 | Konig et al. | 260/239.1 |

FOREIGN PATENT DOCUMENTS 7,407,815   12/1974   Netherlands ............... 260/243 C Primary Examiner—Nicholas S. Rizzo
Attorney, Agent, or Firm—William B. Scanlon; Everet F. Smith

[57] ABSTRACT

Cephalosporin compounds represented by the formula

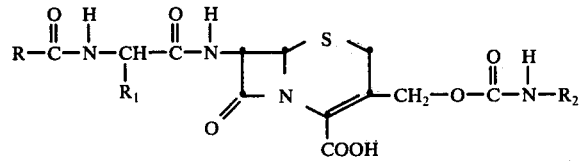

wherein R is an acylamino group

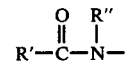

and R' is for example phenyl or furyl, R" is H or CH₃; or R is a substituted ureido group

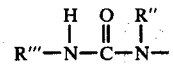

and R" is H or CH₃, R'" is e.g., $C_1$–$C_3$ alkyl; or R is a cyclic ureido group, e.g., imidazolidine-2-one-1-yl and wherein $R_1$ is phenyl, substituted phenyl, thienyl, or furyl; are broad spectrum antibiotics exhibiting an expanded spectrum of activity vs. gram-negative microorganisms.

8 Claims, No Drawings

7-SUBSTITUTED-UREIDO-3-CARBAMOYLOX-YMETHYL CEPHALOSPORIN ANTIBIOTICS

BACKGROUND OF THE INVENTION

Certain cephalosporin compounds having a ureido or a substituted ureido substituent in the α-position of the 7-acylamido side chain have been described. For example, in U.S. Pat. No. 3,673,183 and British Pat. No. 1,337,000, α-ureidocephalosporanic acids are taught. Acyloxymethyl esters of α-ureidocyclohexadienylacetamidocephalosporins are described by U.S. Pat. No. 3,708,479 and such esters of α-aminobenzylpenicillin are described in U.S. Pat. No. 3,697,507. Likewise, penicillins and cephalosporins having an α-(3-imidoylureido)arylacetamido side chain are described in U.S. Pat. Nos. 3,634,405 and 3,646,024, respectively. 7-(α-3-Acylureidophenyl) or thienyl(acetamido)cephalosporanic acids are described by U.S. Pat. No. 3,687,949. Also, Netherlands published application No. 7407815 describes certain 7-α -acylureidophenylacetamidocephalosporin compounds having an acetoxymethyl group, a 1-methyl-1H-tetrazole-5-ylthiomethyl group, a 2-methyl-1,3,4-thiadiazole-5-ylthiomethyl group, and certain other groups substituted in the 3-position.

The cephalosporin class of antibiotics has achieved wide acceptance in the treatment of infectious diseases. Although the cephalosporin antibiotics are recognized as having a broad spectrum of activity, certain microorganisms of the gram-negative class are difficult to control. Accordingly, research efforts continue to develop cephalosporin antibiotics useful in the control of such gram-negative organisms as the Pseudomonas, Serratia, and Klebsiella.

This invention relates to cephalosporin antibiotics having an enhanced activity against gram-negative microorganisms. In particular, this invention relates to cephalosporin antibiotics substituted in the 7-position by an arylacetamido group bearing a substituted α-ureido substituent and in the 3-position by a carbamoyloxymethyl substituent.

DETAILED DESCRIPTION

The cephalosporin antibiotic compounds of this invention are represented by the following structural formula

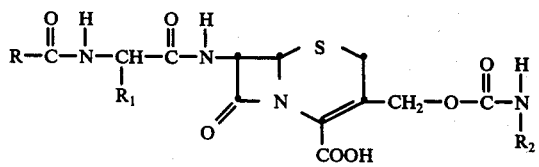

wherein R is an acylamino group of the formula $$R'-\overset{\overset{O}{\|}}{C}-\overset{\overset{R''}{|}}{N}-$$

wherein R' is $C_1$–$C_4$ alkyl, furyl, thienyl, phenyl, phenyl substituted by $C_1$–$C_4$ lower alkyl, $C_1$–$C_4$ lower alkoxy, halogen, or nitro; styryl, or styryl optionally substituted on phenyl by $C_1$–$C_4$ lower alkyl, $C_1$–$C_4$ lower alkoxy, halogen or nitro; and R" is hydrogen or methyl;

or R is a substituted ureido group of the formula

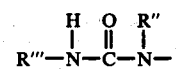

wherein R" is hydrogen or methyl, and R''' is $C_1$–$C_3$ alkyl, allyl, phenyl, benzyl, or furfuryl, or R is a cyclic ureido group of the formula

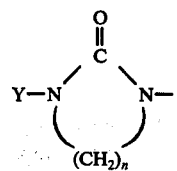

wherein
Y is $C_2$–$C_4$ alkanoyl or $C_1$–$C_3$ alkylsulfonyl, and
n is 1 or 2;
$R_1$ is phenyl, phenyl substituted by $C_1$–$C_4$ lower alkyl, $C_1$–$C_4$ lower alkoxy, halogen, hydroxy or nitro;

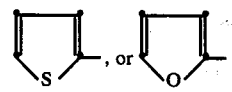

$R_2$ is hydrogen or $C_1$–$C_3$ alkyl;
and the pharmaceutically acceptable non-toxic salts thereof.

In the foregoing description of the compounds of the invention, the term "$C_1$–$C_4$ alkyl" refers to methyl, ethyl, n-propyl, isopropyl, n-butyl, sec-butyl, and t-butyl; "$C_1$–$C_4$ lower alkoxy" refers to methoxy, ethoxy, isopropoxy, n-butoxy and like groups; and "halogen" refers to fluoro, chloro or bromo. Illustrative substituted phenyl groups defined above include for example the $C_1$–$C_4$ lower alkyl substituted phenyl groups such as 4-methylphenyl, 3-methylphenyl, 2-methylphenyl, 4-ethylphenyl, 3-ethylphenyl, 4-n-butylphenyl 3,4-dimethylphenyl, mesityl, 3-methyl-4-ethylphenyl, and the like; the lower alkoxy substituted phenyl groups such as 4-methylphenyl, 2-methoxyphenyl, 3-methoxyphenyl, 4-isopropoxyphenyl, 3,4-dimethoxyphenyl, 2-ethoxyphenyl, 3-ethoxyphenyl, 3-methoxy-4-ethoxyphenyl, 4-n-butoxyphenyl and the like; halo substituted phenyl includes for example, 2-chlorophenyl, 3-chlorophenyl, 4-bromophenyl, 3-bromophenyl, 4-fluorophenyl, 3,4-dichlorophenyl, 2,4-dichlorophenyl, and the like; nitro substituted phenyl refers to the o, m and p-nitrophenyl groups; hydroxy substituted phenyl refers to 4-hydroxyphenyl, 3-hydroxyphenyl, 2-hydroxyphenyl, 3,4-dihydroxyphenyl and the like; and to the substituted phenyl groups wherein different substituents are present such as 3-chloro-4-methylphenyl, 3-chloro-4-hydroxyphenyl, 4-methoxy-3-hydroxyphenyl, 4-chloro-3-methoxyphenyl and the like. Substituted styryl groups include for example, 4-chlorostyryl, 3,4-dichlorostyryl, 3-bromostyryl, 4-methoxystyryl, 3,4-dimethoxystyryl, 3,4-dimethylstyryl, 4-isopropylstyryl, 4-methyl-3-chlorostyryl and the like.

Preferred substituted phenyl groups represented by R' in the above formula are chlorophenyl such as 2- and 4-chlorophenyl, and nitrophenyl. Preferred substituted styryl groups are chlorostyryl such as 2- or 4-chlorostyryl, and nitrostyryl.

The term "$C_1$-$C_3$ alkylsulfonyl" refers to methylsulfonyl, ethylsulfonyl and n-propylsulfonyl.

Preferred substituted phenyl groups represented by $R_1$ in the above formula are hydroxyphenyl and chloro substituted hydroxyphenyl. Illustrative of the preferred substituted phenyl groups of the formula

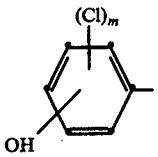

are the o, m, and p-hydroxyphenyl groups; the monochloro, monohydroxy-substituted phenyl groups such as 2-chloro-4-hydroxyphenyl, 3-chloro-4-hydroxyphenyl, 4-chloro-3-hydroxyphenyl, 4-chloro-2-hydroxyphenyl, and the dichloro substituted monohydroxyphenyl groups such as 3,5-dichloro-4-hydroxyphenyl.

The cyclic ureido group represented by R in the above formula are the 5-membered imidazolidine-2-one-1-yl group ($n = 2$) and the 6-membered hexahydropyrimidine-2-one-1-yl group which are represented respectively by the following formulas

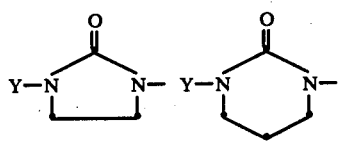

wherein Y is H-, $C_1$-$C_3$ alkylsulfonyl, and $C_2$-$C_4$ alkanoyl.

The compounds of the invention represented by the above formula I are prepared by the acylation of the α-amino group of the 7-position side chain of a 7-(α-amino-α-aryl-acetamido)-3-carbamoyloxymethyl-3-cephem-4-carboxylic acid represented by the following formula II

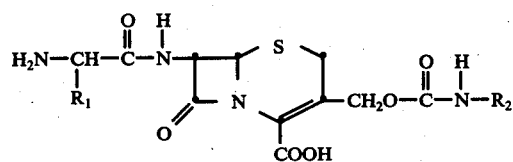

wherein $R_1$ and $R_2$ have the same meanings as defined previously.

The compounds of the formula I wherein R represents an acylamino group of the formula

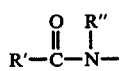

are prepared by reacting the starting material represented by the formula II with an isocyanate of the following formula

wherein R' has the same meanings as defined above, to provide the 7-(3-acyl-1-ureido)-α-arylacetamido-3-carbamoyloxymethyl-3-cephem-4-carboxylic acid compound represented by the formula I wherein R" is hydrogen. The corresponding 3-acyl-3-methyl-1-ureido compounds wherein R" is methyl are prepared by reacting the starting material of the formula II with an N-acyl-N-methylcarbamoyl chloride represented by the formula

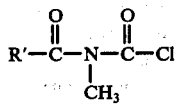

wherein R' again has the same meanings as previously defined.

Illustrative of the isocyanates which can be used to prepare the compounds of the formula I wherein R" is hydrogen are 2-furoyl isocyanate, 2-thenoyl isocyanate, benzoyl isocyanate, 4-chlorobenzoyl isocyanate, 2-chlorobenzoyl isocyanate, 4-nitrobenzoyl isocyanate, cinnamoyl isocyanate, 2-chlorocinnamoyl isocyanate, and 4-nitrocinnamoyl isocyanate.

In a specific embodiment of the preparation of a compound of the formula I wherein R" is hydrogen, furoyl isocyanate is reacted in an inert solvent, for example acetonitrile, with 7-(D-α-aminophenylacetamido)-3-carbamoyloxymethyl-3-cephem-4-carboxylic acid at a temperature of about 0° to 5° C. to provide 7-[D-α-(3-α-furoyl-1-ureido)phenylacetamido]-3-carbamoyloxymethyl-3-cephem-4-carboxylic acid. A large excess of 2-furoyl isocyanate is best employed in the reaction which is carried out under essentially anhydrous conditions. In general, the starting materials of the formula II such as the above-named starting material are not readily soluble in such solvents as acetonitrile and methylene chloride. Accordingly, a convenient method for forming solutions of these starting materials employs the use of a silylating agent such as bis-trimethylsilylacetamide (BSA). Accordingly, a suspension of the starting material in the reaction solvent for example acetonitrile is treated with sufficient BSA to form a soluble silylated starting material. Following addition of the isocyanate, the reaction mixture is stirred for about 1 hour in the cold and is then stirred at about room temperature. The reaction mixture is filtered and excess isocyanate is decomposed by the addition of an alcohol such as methyl alcohol. The reaction mixture is concentrated to a small volume and the reaction product is extracted with ethyl acetate from the concentrate at a pH of about 2.

As mentioned above, the compounds of the formula I wherein R" is methyl are prepared by reacting the above-described N-acyl-N-methylcarbamoyl chloride with a compound of the formula II. Illustrative carbamoyl chlorides which are employed to prepare the compounds of the invention are N-(α-furoyl)-N-methylcarbamoyl chloride, N-(α-benzoyl)-N-methylcarbamoyl chloride, N-(2-chlorobenzoyl)-N-methylcarbamoyl chloride, N-cinnamoyl-N-methylcarbamoyl chloride, N-acetyl-N-methylcarbamoyl chloride, N-(2-chlorocinnamoyl)-N-methylcarbamoyl chloride, and N-(4-nitrocinnamoyl)-N-methylcarbamoyl chloride.

The N-methylcarbamoyl chlorides are readily prepared by reacting the N-methyl amide of the corresponding acid, for example N-methylbenzamide or N-methyl-2-furamide, with an organolithium compound, for example n-butyl lithium at a temperature of about 78° C. to generate the lithium salt of the amide. The lithium salt of the amide is then reacted with phosgene in the cold to provide the carbamoyl chloride. The reaction with phosgene is carried out in the cold at about −78° C. in an inert solvent such as tetrahydrofuran.

The acylation of the starting material of the formula II with the N-carbamoyl chloride is carried out in an inert solvent at a temperature of about −15° and 10° C. in the presence of a hydrogen halide acceptor. Inert solvents such as acetonitrile and tetrahydrofuran are suitable in the reaction. Hydrogen halide acceptors such as the tertiary amines, triethylamine, and pyridine as well as the alkylene oxides such as propylene oxide and butylene oxide can be used. In general, equimolar amounts of the starting material and the N-methylcarbamoyl chloride are employed. In an example of the preparation of a compound of the formula I wherein R'' is methyl, 7-(D-α-amino-α-phenylacetamido)-3-carbamoyloxymethyl-3-cephem-4-carboxylic acid is suspended in acetonitrile containing excess propylene oxide. A small amount of a silylating agent such as bis-trimethylsilylacetamide is added to solubilize the cephalosporin starting material. The solution is cooled to a temperature of about −15° to 0° C. and an equivalent amount of N-cinnamoyl-N-methylcarbamoyl chloride in solution in a small volume of acetonitrile is added with stirring. The reaction mixture is agitated for between 1 and 3 hours in the cold and for about 1 hour at room temperature and is then diluted with a mixture of water and ethyl acetate. The pH of the mixture is adjusted to about 8.5 and the organic layer is separated from the aqueous layer. The product, 7-[D-α-(3-cinnamoyl-3-methyl-1-ureido)-α-phenylacetamido]-3-carbamoyloxymethyl-3-cephem-4-carboxylic acid, is extracted from the aqueous phase at pH 2.5 with an organic solvent such as ethyl acetate.

The compounds of the invention of formula I wherein R is a substituted ureido group of the formula

and R'' is methyl are prepared by acylating a 7-arylglycylamidocephalosporin starting material of the formula II with the N-methylcarbamoyl chloride of the formula

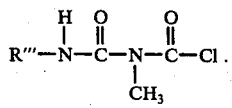

The carbamoyl chlorides of the above formula are prepared by reacting the 1,3-disubstituted urea with phosgene in a dry, inert solvent, for example dichloroethane, dichloromethane, or tetrahydrofuran. The reaction is preferably carried out in the cold at a temperature of about 0° C. When the urea starting material is unsymmetrical, for example when R''' is a group other than methyl, the unsymmetrical urea is capable of forming two carbamoyl chlorides on reaction with phosgene. The desired N-methylcarbamoyl chloride of the formula

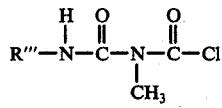

can be separated from the undesired isomer by fractional crystallization from mixtures of polar and nonpolar solvents such as mixtures of diethyl ether and petroleum ether and acetone, and ethyl acetate and hexane or petroleum ether.

Examples of carbamoyl chlorides defined above are N-methylaminocarbonyl-N-methylcarbamoyl chloride, N-phenylaminocarbonyl-N-methylcarbamoyl chloride, N-furfurylaminocarbonyl-N-methylcarbamoyl chloride, N-benzylaminocarbonyl-N-methylcarbamoyl chloride, N-allylaminocarbonyl-N-methylcarbamoyl chloride, and N-ethylaminocarbonyl-N-methylcarbamoyl chloride.

The compounds of the invention represented by formula I wherein R is a substituted ureido group and R'' is hydrogen are prepared by reacting the 7-arylglycylamido starting material of the formula II with the p-nitrophenyl carbamate of the formula

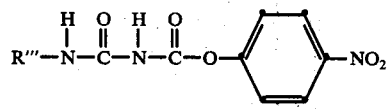

The p-nitrophenylcarbamates of the above formula are prepared by reacting the 3-disubstituted urea of the formula

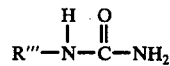

with p-nitrophenyl chloroformate. The reaction of the urea with the chloroformate is carried out in an inert solvent, for example tetrahydrofuran at a temperature of about 0° C.

The monosubstituted urea represented can react with the chloroformate to form isomeric p-nitrophenyl carbamates, since both nitrogens of the urea are available for reaction with the chloroformate. The desired carbamate is formed by the acylation of the $N_1$ (unsubstituted) urea nitrogen, while the undesired carbamate is formed by the acylation of the $N_3$ (substituted) urea nitrogen. Commonly, the two products are formed in about equal amounts.

The desired p-nitrophenyl carbamate can be converted to the corresponding isocyanate upon treatment with a silylating agent such as bis-(trimethylsilyl)acetamide or a mono-(trimethylsilyl)acetamide. The undesired isomer, i.e. formed by the reaction on the nitrogen bearing the substituent group, is incapable of forming an isocyanate with a silylating agent. Accordingly, advantage is taken of this selective formation of an isocyanate from the carbamate ester to obtain the desired acylation product on reaction with the starting material of formula II. The reaction of the p-nitrophenyl carbamate esters with silylating agents has been previously described in Angew. Chem. Int. Ed., XVII (1968) 941 and is illustrated by the following reaction scheme:

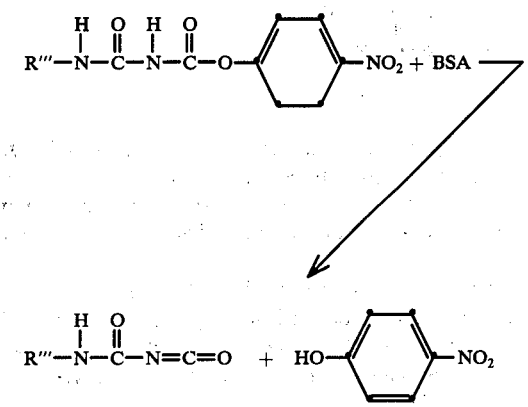

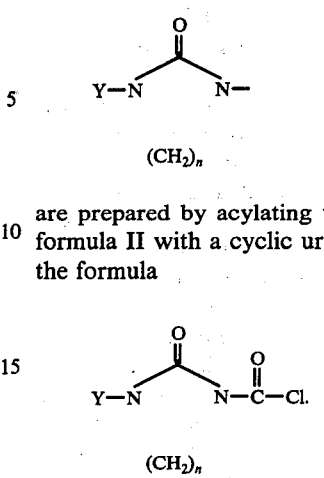

As noted above, the undesired isomer, i.e., the carbamate prepared by the reaction of the chloroformate with the nitrogen bearing the R''' substituent is incapable of forming an isocyanate with a silylating agent. Accordingly, in the preparation of a compound of the formula I the mixture of p-nitrophenyl carbamates can be reacted in situ with a silylating agent, thus converting the desired isomer to the isocyanate. The isocyanate then reacts with the α-amino group of the starting material of the formula II to provide the desired product. Accordingly, in the acylation of a 7-glycylamidocephalosporin of the formula II the mixture of both carbamates obtained as described above is conveniently used. The acylation reaction is carried out in an inert solvent under substantially anhydrous conditions in the presence of an excess of a silylating agent such as BSA or MSA.

To illustrate the preparation of a compound of the formula I wherein R is a substituted ureido group wherein both R'' is hydrogen and R''' is methyl, 7-(D-α-amino-α-phenylacetamido)-3-carbamoyloxymethyl-3-cephem-4-carboxylic acid was suspended in dry acetonitrile and excess BSA was added. To the solution containing excess BSA was added a mixture of the isomeric p-nitrophenyl carbamates obtained by the reaction of N-methyl urea with p-nitrophenyl chloroformate. The reaction mixture is then agitated for between 1 and 3 hours, is then diluted with an alcohol such as methyl or ethyl alcohol to affect the decomposition of any excess isocyanate and is then evaporated to dryness in vacuo. The residual reaction product mixture is taken up in an organic solvent such as ethyl acetate and is filtered to remove the insoluble side products. The filtrate is evaporated to afford the product 7-[D-α-(3-methylcarbamoyl-1-ureido)-α-phenylacetamido]-3-carbamoyloxymethyl-3-cephem-4-carboxylic acid as a solid residue. The product can be purified by recrystallization or trituration with an organic solvent.

Examples of p-nitrophenyl carbamates useful in preparing the compounds of the formula I wherein R'' is hydrogen include p-nitrophenyl N-(methylcarbamoyl)-carbamate, p-nitrophenyl N-(ethylcarbamoyl)carbamate, p-nitrophenyl N-(allylcarbamoyl)carbamate, p-nitrophenyl N-(phenylcarbamoyl)carbamate, p-nitrophenyl N-(benzylcarbamoyl)carbamate, p-nitrophenyl N-(furfurylcarbamoyl)carbamate, and like carbamates.

The compounds of the formula I wherein R is a cyclic ureido group represented by the formula are prepared by acylating the starting material of the formula II with a cyclic ureido carbamoyl chloride of the formula The acylation is carried out by following the procedures and employing the conditions described above for the acylation with the acyclic carbamoyl chlorides.

The cyclic ureido carbamoyl chlorides of the above formula wherein Y and n are as defined previously are prepared by reacting the substituted (Y = $C_2$-$C_4$ alkanoyl or $C_1$-$C_3$ alkylsulfonyl) or unsubstituted (Y = H) imidazolidine-2-one (n = 2) or hexahydropyrimidine-2-one (n = 3) with phosgene in an inert solvent under substantially anhydrous conditions at a temperature of about 0° to 10° C.

PREPARATION OF STARTING MATERIALS

The 7-(α-amino-α-arylacetamido)-3-carbamoyloxymethyl-3-cephem-4-carboxylic acids represented by the formula II wherein $R_2$ is hydrogen can be prepared by the method described by Webber in U.S. Pat. No. 3,905,963. Alternatively, they can be prepared by the acylation of 7-amino-3-carbamoyloxymethyl-3-cephem-4-carboxylic acid obtained as follows. 7-Aminocephalosporanic acid (7ACA) is first reacted with the mixed anhydride of acetic acid and formic acid to form the 7-β-formamido (N-formyl) derivative. The 7-β-formamido derivative is then deacetylated, for example with the deacylase produced by *Bacillus subtilis* or by chemical hydrolysis to form 7-β-formamido-3-hydroxymethyl-3-cephem-4-carboxylic acid. The desacetyl 7-β-formamido product is then O-acylated with trichloroacetylisocyanate to provide the intermediate, 7-β-formamido-3-(N-trichloroacetylcarbamoyloxymethyl)-3-cephem-4-carboxylic acid. This intermediate is hydrolyzed with aqueous sodium bicarbonate to effect the hydrolysis of the N-trichloroacetyl group in the 3'-position and form 7-β-formamido-3-carbamoyloxymethyl-3-cephem-4 carboxylic acid. The N-formyl group is then hydrolyzed with hydrochloric acid in methanol to yield 7-amino-3-carbamoyloxymethyl-3-cephem-4-carboxylic acid.

The acylation of the 7-amino group of the above 3-carbamoyloxymethyl nucleus compound to obtain a compound of the formula II is carried out by conventional N-acylation procedures with an amino-protected arylglycine. For example, the amino group of phenylglycine or a substituted phenylglycine represented by the formula

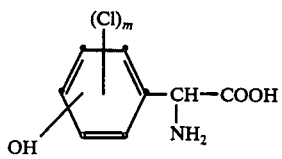

is first protected with one of the commonly used amino protecting groups such as those forming urethanes for example the t-butyloxycarbonyl, p-nitrobenzyloxycarbonyl, and 2,2,2-trichloroethoxycarbonyl groups, or by formation of an enamine with, for example ethyl acetoacetate, methyl acetoacetate, or acetylacetone, or alternatively, the amino group can be protected via salt formation such as by forming the hydrochloride salt of the phenyl, substituted phenyl, thienyl, or furyl glycine. The amino-protected arylglycine is then converted to a reactive carboxylic acid derivative for use in the acylation of the 7-amino nucleus compound. Reactive carboxylic acid derivatives such as the acid chloride, acid azide, an anhydride, or an active ester, for example the active ester formed with ethyl chloroformate, can be used to acylate the 7-amino-3-carbamoyloxymethyl (or $C_1$–$C_3$alkylcarbamoyloxymethyl)-3-cephem-4-carboxylic acid nucleus. Subsequent to the acylation, the aminoprotecting group is removed to provide the starting material of the formula II.

Representative arylglycylamido substituted cephalosporins of the formula II which are useful starting materials for the preparation of the compounds of the invention are shown in the following Table I.

Table I

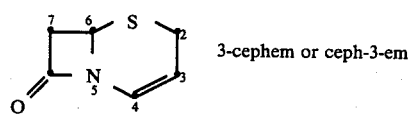

| $R_1$ | $R_2$ |
|---|---|
| phenyl | H |
| 4-hydroxyphenyl | H |
| " | CH₃ |
| 3-hydroxyphenyl | H |
| " | CH₃ |
| 4-chloro-3-hydroxyphenyl | H |
| " | C₂H₅ |
| 3,5-dichloro-4-hydroxyphenyl | H |
| " | CH₃ |
| 3-chlorophenyl | H |
| " | n-C₃H₇ |
| 4-chlorophenyl | CH₃ |
| " | H |
| phenyl | CH₃ |
| " | n-C₃H₇ |
| 2-hydroxyphenyl | iso-C₃H₇ |
| 2-chlorophenyl | H |
| 3,4-dichlorophenyl | H |
| 3-hydroxy-4-chlorophenyl | H |
| " | CH₃ |
| 2-thienyl | H |
| " | CH₃ |
| 2-furyl | H |
| " | CH₃ |

Table I-continued

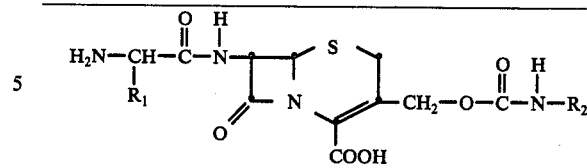

| $R_1$ | $R_2$ |
|---|---|
| " | C₂H₅ |

The cephalosporin compounds described herein are named according to the cepham nomenclature system which employs the basic cephem ring system consisting of a β-lactam ring fused to a six-membered dihydrothiazine ring.

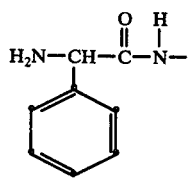 3-cephem or ceph-3-em

The 7-acylamido group attached to the β-lactam ring is named herein in the following manner as illustrated with $R_1$ = phenyl of the side chain:

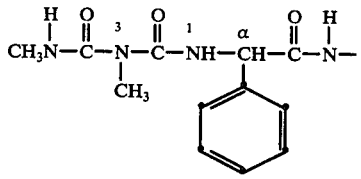

"phenylglycylamido" or α-amino-α-phenylacetamido

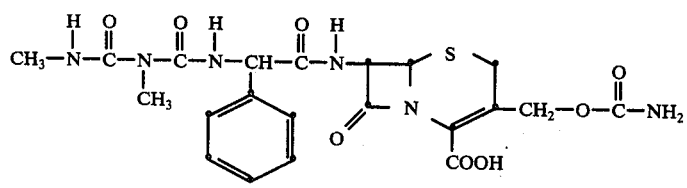

"7-[α-(3-methylcarbamoyl-3-methyl-1-ureido)-α-phenylacetamido]-"

The "α" refers to the carbon atom of the acetamido group to which is attached the phenyl group, while the numerals refer to the nitrogen atoms in the indicated urea moiety. Accordingly, the following structural formula representing a compound of the invention is named, 7-[α-(3-methylcarbamoyl-3-methyl-1-ureido)-α-phenylacetamido]-3-carbamoyloxymethyl-3-cephem-4-carboxylic acid. Alternatively, the above compound can be named formally as a carbamic acid ester as follows: 3-(hydroxymethyl)-7-[2-[(3-methyl-3-methylcarbamoyl)ureido]-2-phenylacetamido]-3-cephem-4-carboxylic acid, carbamate (ester).

The α-carbon atom of the 7-arylglycylamido side chain is assymetric and retains its initial configuration when acylated to form the substituted ureido compounds of the invention. The preferred compounds of the invention are prepared with the D-arylglycylamido cephalosporin.

Illustrative of the compounds of the invention represented by the formula I wherein R is an acylamino group

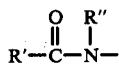

are: 7-[D-α-(3-acetyl-1-ureido)-α-phenylacetamido]-3-carbamoyloxymethyl-3-cephem-4-carboxylic acid, 7-[D-α-(3-propionyl-1-ureido)-α-phenylacetamido]-3N-methylcarbamoyloxymethyl-3-cephem-4-carboxylic acid, 7-[D-α-(3-benzoyl-3-methyl-1-ureido)-α-phenylacetamido]-3-carbamoyloxymethyl-3-cephem-4-carboxylic acid, 7-[D-α-(3-o-chlorobenzoyl-3-methyl-1-ureido)-α-(4-hydroxyphenyl)acetamido]-3-carbamoyloxymethyl-3-cephem-4-carboxylic acid, 7-[D-α-(3-cinnamoyl-3-methyl-1-ureido)-α-phenylacetamido]-3-carbamoyloxymethyl-3-cephem-4-carboxylic acid, 7-[D-α-(3-o-nitrocinnamoyl-3-methyl-1-ureido]-α-(3-chloro-4-hydroxyphenyl)acetamido]-3-carbamoyloxymethyl-3-cephem-4-carboxylic acid, 7-[D-α-(3-p-chlorocinnamoyl-3-methyl-1-ureido)-α-(2-thienyl)acetamido]-3-carbamoyloxymethyl-3-cephem-4-carboxylic acid, 7-[D-α-(3-o-chlorobenzoyl-3-methyl-1-ureido)α-phenylacetamido]-3-(N-methylcarbamoyloxymethyl)-3-cephem-4-carboxylic acid, 7-[D-α-(3-cinnamoyl-1-ureido)-α-(3-hydroxyphenyl)acetamido]-3-carbamoyloxymethyl-3-cephem-4-carboxylic acid, 7-[D-α(3-α-furoyl-3-methyl-1-ureido)-α-phenylacetamido]-3-carbamoyloxymethyl-3-cephem-4-carboxylic acid, 7-[D-α-(3-α-furoyl-1-ureido)-α-(4-hydroxyphenyl)acetamido]-3-carbamoyloxymethyl-3-cephem-4-carboxylic acid, 7-[D-α-(3-α-thienoyl-3-methyl-1-ureido)-α-phenylacetamido]-3-carbamoyloxymethyl-3-cephem-4-carboxylic acid, and 7-[D-α-(3-α-thienoyl-1-ureido)-α-(4-hydroxyphenyl)acetamido]-3-carbamoyloxymethyl-3-cephem-4-carboxylic acid.

Examples of compounds of the invention represented by the formula I wherein R is a substituted ureido group

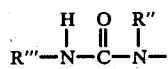

are 7-[D-α-(3-methylcarbamoyl-3-methyl-1-ureido)-α-phenylacetamido]-3-carbamoyloxymethyl-3-cephem-4-carboxylic acid, 7-[D-α-(3-methylcarbamoyl-3-methyl-1-ureido)-α-(4-hydroxyphenyl)acetamido]-3-carbamoyloxymethyl-3-cephem-4-carboxylic acid, 7-[D-α-(3-methylcarbamoyl-3-methyl-1-ureido)-α-(3-chloro-4-hydroxyphenyl)acetamido]-3-carbamoyloxymethyl-3-cephem-4-carboxylic acid, 7-[D-α-(3-methylcarbamoyl-3-methyl-1-ureido)-α-(3-hydroxyphenyl)acetamido]-3-(N-methylcarbamoyloxymethyl)-3-cephem-4-carboxylic acid, 7-[D-α-(3-methylcarbamoyl-3-methyl-1-ureido)-α-(3,5-dichloro-4-hydroxyphenyl)acetamido]-3-carbamoyloxymethyl-3-cephem-4-carboxylic acid, 7-[D-α-(3-methylcarbamoyl-3-methyl-1-ureido)-α-(2-thienyl)acetamido]-3-carbamoyloxymethyl-3-cephem-4-carboxylic acid, 7-[D-α-(3-methylcarbamoyl-3-methyl-1-ureido)-α-(2-furyl)acetamido]-3-carbamoyloxymethyl-3-cephem-4-carboxylic acid, 7-[D-α-(3-methylcarbamoyl-1-ureido)-α-phenylacetamido]-3-carbamoyloxymethyl-3-cephem-4-carboxylic acid, 7-[D-α-(3-methylcarbamoyl-3-methyl-1-ureido)-α-phenylacetamido]-3-(N-methylcarbamoyloxymethyl)-3-cephem-4-carboxylic acid, 7-[D-α-(3-ethylcarbamoyl-3-methyl-1-ureido)-α-(4-chlorophenyl)acetamido]-3-carbamoyloxymethyl-3-cephem-4-carboxylic acid, 7-[D-α-(3-methylcarbamoyl-1-ureido)-α-(2-thienyl)acetamido]-3-(N-n-propylcarbamoyloxymethyl)-3-cephem-4-carboxylic acid, 7-[D-α-(3-n-propylcarbamoyl-3-methyl-1-ureido)-α-phenylacetamido]-3-carbamoyloxymethyl-3-cephem-4-carboxylic acid, 7-[D-α-(3-methylcarbamoyl-1-ureido)-α-(4-hydroxyphenyl)acetamido]-3-(N-methylcarbamoyloxymethyl)-3-cephem-4-carboxylic acid, 7-[D-α-(3-methylcarbamoyl-1-ureido)-α-(2-furyl)acetamido]-3-carbamoyloxymethyl-3-cephem-4-carboxylic acid, and 7-[D-α-(3-methylcarbamoyl-3-methyl-1-ureido)-α-(3,4-dichlorophenyl)acetamido]-3-carbamoyloxymethyl-3-cephem-4-carboxylic acid.

Additional examples of compounds of the invention wherein R of the formula I is a substituted ureido group are 7-[D-α-(3-allylcarbamoyl-3-methyl-1-ureido)-α-phenylacetamido]-3-carbamoyloxymethyl-3-cephem-4-carboxylic acid, 7-[D-α-(3-phenylcarbamoyl-1-ureido)-α-(3-chloro-4-hydroxyphenyl)acetamido]-3-carbamoyloxymethyl-3-cephem-4-carboxylic acid, 7-[D-α-(3-benzylcarbamoyl-3-methyl-1-ureido)-α-(2-furyl)acetamido]-3-carbamoyloxymethyl-3-cephem-4-carboxylic acid, and 7-[D-α-(3-furfurylcarbamoyl-3-methyl-1-ureido)-α-phenylacetamido]-3-carbamoyloxymethyl-3-cephem-4-carboxylic acid.

Examples of compounds described herein wherein R of formula I is a cyclic ureido group include 7-[D-α-(imidazolidine-2-one-1-yl-carbonylamino)-α-phenylacetamido]-3-carbamoyloxymethyl-3-cephem-4-carboxylic acid, 7-[D-α-[3-acetyl)imidazolidine-2-one-1-ylcarbonylamino]-α-(4-hydroxyphenyl)acetamido]-3-carbamoyloxymethyl-3-cephem-4-carboxylic acid, 7-[D-α-[3-(methylsulfonyl)imidazolidine-2-one-1-ylcarbonylamino]-α-(2-thienyl)acetamido]-3-carbamoyloxymethyl-3-cephem-4-carboxylic acid, 7-[D-α-(hexahydropyrimidine-2-one-1-ylcarbonylamino)-α-phenylacetamido]-3-carbamoyloxymethyl-3-cephem-4-carboxylic acid, 7-[D-α-(imidazolidine-2-one-1-ylcarbonylamino)-α-(3-chloro-4-hydroxyphenyl)acetamido]-3-carbamoyloxymethyl-3-cephem-4-carboxylic acid, 7-[D-α-[3-(propionyl)imidazolidine-2-one-1:ylcarbonylamino]-α-(3-hydroxyphenyl)acetamido]-3-carbamoyloxymethyl-3-cephem-4-carboxylic acid, 7-[D-α-[3-(methylsulfonyl)hexahydropyrimidine-2-one-1-ylcarbonylamino]-α-phenylacetamido]-3-(N-methylcarbamoyloxymethyl)-3-cephem-4-carboxylic acid, 7-[D-α-(imidazolidine-2-one-1-ylcarbonylamino)-α-(3,4-dichlorophenyl)acetamido]-3-carbamoyloxymethyl-3-cephem-4-carboxylic acid, 7-[D-α-(hexahydropyrimidine-2-one-1-ylcarbonylamino)-α-phenylacetamido]-3-(N-propylcarbamoyloxymethyl)-3-cephem-4-carboxylic acid, 7-[D-α-[3-(acetyl)hexahydropyrimidine-2-one-1-ylcarbonylamino]-α-(2-thienyl)acetamido]-3-carbamoyloxymethyl-3-cephem-4-carboxylic acid, and 7-[D-α-(imidazolidine-2-one-1-ylcarbonylamino)-α-(2-furyl)acetamido]-3-(N-ethylcarbamoyloxymethyl)-3-cephem-4-carboxylic acid.

Preferred compounds of this invention are the primary carbamates represented by the formula I wherein $R_2$ is hydrogen.

A further preferred group of antibiotics are represented by the formula I wherein R is an "acylamino" group

and R' is 2-furyl, phenyl, chlorophenyl, styryl, chlorostyryl, or nitrostyryl; R" is hydrogen or methyl; $R_2$ is hydrogen and $R_1$ is phenyl, thienyl or

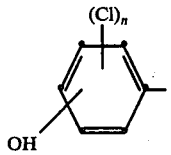

Examples of compounds included with the preferred group are 7-[D-α-(3-α-furoyl-1-ureido)-α-phenylacetamido]-3-carbamoyloxymethyl-3-cephem-4-carboxylic acid, 7-[D-α-(3-α-furoyl-1-ureido)-α-(4-hydroxyphenyl)acetamido]-3-carbamoyloxymethyl-3-cephem-4-carboxylic acid, 7-[D-α-(3-cinnamoyl-1-ureido)-α-phenylacetamido]-3-carbamoyloxylmethyl-3-cephem-4-carboxylic acid, 7-[D-α-(3-cinnamoyl-3-methyl-1-ureido)-α-(3-chloro-4-hydroxyphenyl)acetamido]-3-carbamoyloxymethyl-3-cephem-4-carboxylic acid, and 7-[D-α-(3-o-chlorobenzoyl-3-methyl-1-ureido)-α-phenylacetamido]-3-carbamoyloxymethyl-3-cephem-4-carboxylic acid.

Another preferred group of compounds are represented by the formula I when R is a "substituted ureido" or the "cyclic ureido" group

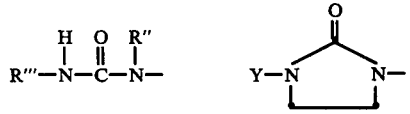

wherein R''' is methyl or phenyl; R" is methyl or hydrogen; $R_1$ is phenyl, thienyl or the preferred substituted phenyl group

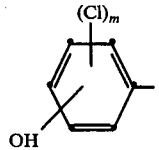

$R_2$ is hydrogen and Y is hydrogen or methylsulfonyl. Examples of this preferred group are 7-[D-α-(3-methylcarbamoyl-3-methyl-1-ureido)-α-phenylacetamido]-3-carbamoyloxymethyl-3-cephem-4-carboxylic acid, 7-[D-α-(3-methylcarbamoyl-3-methyl-1-ureido)-α-(2-thienyl)acetamido]-3-carbamoyloxymethyl-3-cephem-4-carboxylic acid, 7-[D-α-(3-methylcarbamoyl-3-methyl-1-ureido)-α-(4-hydroxyphenyl)acetamido]-3-carbamoyloxymethyl-3-cephem-4-carboxylic acid, 7-[D-α-(3-phenylcarbamoyl-1-ureido)-α-phenylacetamido]-3-carbamoyloxymethyl-3-cephem-4-carboxylic acid, 7-[D-α-(3-methylcarbamoyl-3-methyl-1-ureido)-α-(3-chloro-4-hydroxyphenyl)-acetamido]-3-carbamoyloxymethyl-3-cephem-4-carboxylic acid, 7-[D-α-3-(methylsulfonyl)imidazolidine-2-one-1-ylcarbonylamino]-α-phenylacetamido]-3-carbamoyloxymethyl-3-cephem-4-carboxylic acid, 7-[D-α-[3-(methylsulfonyl)imidazolidine-2-one-1-ylcarbonylamino]-α-(4-hydroxyphenyl)acetamido]-3-carbamoyloxymethyl-3-cephem-4-carboxylic acid, 7-[D-α-(3-imidazolidine-2-one-1-ylcarbonylamino)-α-phenylacetamido]-3-carbamoyloxymethyl-3-cephem-4-carboxylic acid, 7-[D-α-(3-imidazolidine-2-one-1-ylcarbonylamino)-α-(2-thienyl)-acetamido]-3-carbamoyloxymethyl-3-cephem-4-carboxylic acid, and 7-[D-α-(3-methylcarbamoyl-1-ureido)-α-phenylacetamido]-3-carbamoyloxymethyl-3-cephem-4-carboxylic acid.

The cephalosporin antibiotic compounds of this invention form salts with pharmaceutically acceptable bases such as the alkali metal carbonates and bicarbonates for example sodium carbonate, sodium bicarbonate, potassium carbonate and lithium carbonate. Amine salts of the antibiotics are formed with the organic amines such a benzylamine, dibenzylamine, cyclohexylamine, di-n-butylamine, di-(2-hydroxyethyl)amine, procaine, abietylamine, di-(3-hydroxypropylamine, and like amines.

The cephalosporin compounds represented by formula I inhibit the growth of microorganisms pathogenic to man and animals. In particular they are effective in controlling the growth of gram-negative bacteria and penicillin resistant strains of staphylococcus.

The antibiotic activity for these compounds is illustrated by the activity data in the following Table II. In the Table, the compounds designated by the groups R, $R_1$ and $R_2$ have reference to the following formula I

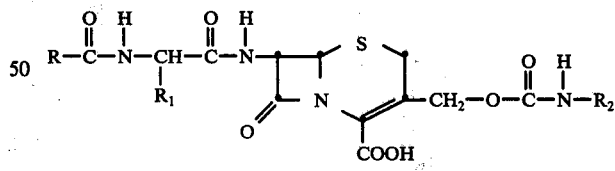

and the in vitro activity was determined by the Gradient Plate method.

TABLE II

7-Substituted-Ureido-3-Carbamoyloxymethyl Cephalosporins
In Vitro Antibiotic Activity vs. Gram-Negative Bacteria

| Test Compounds | | | Minimum Inhibitory Concentration (mcg/ml) vs. | | | | | | |
|---|---|---|---|---|---|---|---|---|---|
| R | $R_1$ | $R_2$ | Shigella sp. | Escherichia coli | Klebsiella pneumoniae | Enterobacter aerogenes | Salmonella heidelberg | Pseudomonas aeruginosa | Serratia marcescens |
| φ-CH=CH-C(O)-N(CH₃)- | phenyl | H | 1.0 | 5.5 | 0.3 | 8.0 | 6.5 | 21.8 | 8.0 |

TABLE II-continued

7-Substituted-Ureido-3-Carbamoyloxymethyl Cephalosporins
In Vitro Antibiotic Activity vs. Gram-Negative Bacteria

| Test Compounds R | $R_1$ | $R_2$ | Shigella sp. | Escherichia coli | Klebsiella pneumoniae | Enterobacter aerogenes | Salmonella heidelberg | Pseudomonas aeruginosa | Serratia marcescens |
|---|---|---|---|---|---|---|---|---|---|
| 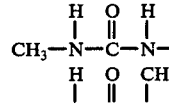 | 4-hydroxyphenyl | H | 17.3 | 27.2 | 100 | 18.5 | 12.5 | 33.3 | >200 |
| 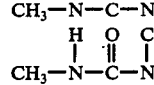 | 4-hydroxyphenyl | H | 4.5 | 10.0 | 10.0 | 5.5 | 5.0 | 13.5 | 160 |
| 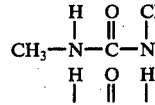 | phenyl | H | 7.0 | 17.8 | 7.8 | 19.5 | 8.5 | 18.3 | 67.5 |
| 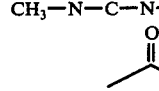 | phenyl | $CH_3$ | 5.5 | 15.5 | 7.0 | 19.5 | 8.5 | 30 | 42.5 |
| 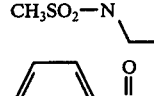 | phenyl | H | 21.5 | 51.3 | 35 | 65 | 30 | 22.8 | >200 |
| 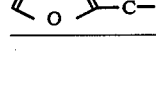 | 4-hydroxyphenyl | H | 4.3 | 10.0 | 5.5 | 10.0 | 4.8 | 47.5 | 100 |
| 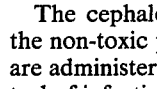 | 4-hydroxyphenyl | H | 12.5 | 17.2 | 16 | 17.2 | 16 | 10 | 120 |

The cephalosporin antibiotics of this invention and the non-toxic pharmaceutically acceptable salts thereof are administered parenterally in the treatment and control of infectious diseases. For example they are administered via the instramuscular or intravenous route in suitable formulations such as sterile solutions in water or isotonic saline, or as solutions in dextrose or other commonly used i.v. fluid.

This invention is further illustrated by the following examples.

EXAMPLE 1

7-[a-(3-Methylcarbamoyl-3-methyl-1-ureido)-α-phenylacetamido]-3-carbamoyloxymethyl-3-cephem-4-carboxylic acid.

To a suspension of 3.15 g. of 7-(D-α-amino-α-phenylacetamido)-3-carbamoyloxymethyl-3-cephem-4-carboxylic acid in 62 ml. of dry acetonitrile containing 15.5 ml. of propylene oxide were added 7.74 ml. of bis-(trimethylsilyl)acetamide. When a homogeneous solution was obtained, the solution was cooled to a temperature of about 0° C. and a solution of 1.16 g. of N-methylaminocarbonyl-N-melthylcarbamoyl chloride in 15 ml. of dry acetonitrile was added. The reaction mixture was stirred for 2 hours in the cold and allowed to warm to room temperature. The mixture was poured into a mixture of ethyl acetate and water and the pH of aqueous phase adjusted to about pH 9. The aqueous layer was separated and relayered with fresh ethyl acetate. The pH of the aqueous layer was adjusted to 2.5 and the ethyl acetate layer was separated, washed with brine and dried over sodium sulfate. The dried solution containing the product was evaporated to dryness under vacuum to yield 1.5 g. of an off-white crystalline solid. A small portion of the product was recrystallized from methylene chloride-methyl alcohol containing a few drops of isopropyl alcohol.

Elemental analysis for $C_{21}H_{24}N_6O_8S_1$: Theory: C, 48.46; H, 4.65; N, 16.15; Found: C, 47.94; H, 3.86; N, 15.39.

EXAMPLE 2

7-[α-(3-Methylcarbamoyl-3-methyl-1-ureido)-α-phenylacetamido]-3-N-methylcarbamoyloxymethyl-3-cephem-4-carboxylic acid.

To 12 ml. of dry acetonitrile were added 225 mg. of N-methylaminocarbonyl-N-methylcarbamoyl chloride, 3 ml. of propylene oxide and 1.5 ml. of BSA. The solution was cooled to 0° C. and 630 g. of 7-(D-α-amino-α-phenylacetamido)-3-N-methylcarbamoyloxymethyl-3-cephem-4-carboxylic acid were added with stirring. The solution was stirred for 2 hours without external cooling to allow the temperature of the reaction mixture to warm gradually to about room temperature. As the reaction proceeded, a clear solution was formed. The reaction mixture was poured into a mixture of water and ethyl acetate and the pH was adjusted to 8.5 with sodium bicarbonate. The ethyl acetate layer was separated and discarded. The aqueous phase was relayered with fresh ethyl acetate and the pH adjusted to 2.5 with sulfuric acid. Due to the formation of an emulsion, the ethyl acetate layer was separated and the emulsion was relayered with fresh ethyl acetate. The pH was intially adjusted to 8 with sodium bicarbonate and finally back to pH 2.5 by the slow addition of hydrochloric acid. The ethyl acetate layer was separated and the aqueous layer extracted twice with ethyl acetate. The extracts were combined with the previously separated ethyl acetate layers and the whole was washed with brine and dried over sodium sulfate. Evaporation of the dried ethyl acetate solution of the product under vacuum yielded the product as a white solid residue. The product was dissolved in tetrahydrofuran and the solution was diluted with diethyl ether and placed in a freezer for crystallization. The product crystallized, was filtered and air dried. Yield: 168 mg. melting at about 180°–183° C.

Elemental analysis for $C_{22}H_{26}N_6O_8S_1$: Theory: C, 49.43; H, 4.90; N, 15.72; Found: C, 49.76; H, 5.26; N, 15.41.

EXAMPLE 3

7-[α-(3-Methylcarbamoyl-1-ureido)-α-phenylacetamido]-3-carbamoyloxymethyl-3-cephem-4-carboxylic acid.

To a suspension of 1.04 g. of 7-(D-α-amino-α-phenylacetamido)-3-carbamoyloxymethyl-3-cephem-4-carboxylic acid trifluoroacetate salt in 16 ml. of dry acetonitrile at room temperature were added 2 ml. of BSA and 1.8 g. of p-nitrophenyl methylcarbamoylcarbamate. The mixture was stirred at room temperature for one hour and was poured into ethyl acetate/water. The pH of the aqueous layer was adjusted to 6 and the ethyl acetate layer was separated. The aqueous layer was relayered with fresh ethyl acetate and the pH adjusted to pH 2.5. The organic phase was separated, washed with brine, dried and evaporated to yield 144 mg. of the product as a residual white solid.

Elemental analysis for $C_{20}H_{22}N_6O_8S_1$: Theory: C, 47.43; H, 4.38; N, 16.59; Found: C, 47.25; H, 4.72; N, 16.38.

EXAMPLE 4

7-[D-α-(3-Methylcarbamoyl-3-methyl-1-ureido)-α-(4-hydroxyphenyl)acetamido]-3-carbamoyloxymethyl-3-cephem-4-carboxylic acid.

The title compound was prepared when by following the reaction conditions and work-up procedures of Example 1, two millimoles of the trifluoroacetate salt of 7-(D-α-amino-α-phenylacetamido)-3-carbamoyloxymethyl-3-cephem-4-carboxylic acid was reacted in 16 ml. of dry acetonitrile with two millimoles of N-methylaminocarbonyl-N-methylcarbamoyl chloride in the presence of 4 ml. of propylene oxide and 2 ml. of BSA. The yield of product obtained was 220 mg.

EXAMPLE 5

7-[D-α-(3-methylcarbamoyl-1-ureido)-α-(4-hydroxyphenyl)acetamido]-3-carbamoyloxymethyl-3-cephem-4-carboxylic acid.

Two millimoles (1.02 g.) of 7-[D-α-amino-α-(4-hydroxyphenyl)acetamido]-3-carbamoyloxymethyl-3-cephem-4-carboxylic acid was dissolved in 16 ml. of dry acetonitrile and 2 ml. of BSA were added. The solution was stirred and 1.8 g. of p-nitrophenyl methylcarbamoylcarbamate were added. After the reaction mixture was stirred at room temperature for one hour, 5 ml. of methyl alcohol were added and the mixture was evaporated under vacuum. The solid residue was dissolved in ethyl acetate, the solution was filtered and then evaporated under vacuum. The product, as the solid residue, was thoroughly triturated with diethyl ether and filtered to yield 880 mg.

EXAMPLE 6

7-[D-α-[3-(methylsulfonyl)imidazolidine-2-one-1-ylcarbonylamino]-α-(4-hydroxyphenyl)acetamido]-3-carbamoyloxymethyl-3-cephem-4-carboxylic acid.

To a suspension of 758 mg. of sodium α-[3-(methylsulfonyl)imidazolidine-2-one-1-ylcarbonylamino]phenylacetate in 20 ml. of dry tetrahydrofuran were added 342 mg. of N-trimethylsilylsuccinimide. The suspension was stirred for 30 min. and 2 drops of dimethylbenzylamine and 0.28 ml. of isobutylchloroformate were added. The solution was stirred for 15 min. and cooled to −22° C. A solution of 682 mg. of 7-amino-3-carbamoyloxymethyl-3-cephem-4-carboxylic acid in dry tetrahydrofuran containing 2.5 ml. of BSA was added to the cold solution. The reaction mixture was stirred for one hour at −22° C., two hours at 0° C., and then allowed to warm to room temperature. Ten milliliters of methyl alcohol were added and the mixture was filtered to remove insolubles. The filtered reaction mixture was evaporated to a volume of 10 ml. and 50 ml. of a 1:1 (v:v) mixture of ethyl acetate water were added. The pH was adjusted to 2 and the ethyl acetate layer separated. The aqueous phase was extracted with ethyl acetate and the extract combined with the previously separated organic layer. The ethyl acetate solution containing the product was washed with water, dried, and evaporated to yield 1.09 g. of product. The product was crystallized from acetone and was obtained as intensely yellowish-orange crystals.

EXAMPLE 7

7-[D-α-(3-α-Furoyl-1-ureido)-α-(4-hydroxyphenyl)acetamido]-3-carbamoyloxymethyl-3-cephem-4-carboxylic acid.

A suspension of 500 mg. of 7-[D-α-amino-α-(4-hydroxyphenyl)acetamido]-3-carbamoyloxymethyl-3-cephem-4-carboxylic acid in 100 ml. of dry acetonitrile was sonicated and 1.5 ml. of BSA was added. When solution had occurred, molecular sieve was added and the mixture cooled to about 0° C. A large excess of 2-furoyl isocyanate was added and the reaction mixture was stirred in the cold for one hour. The mixture was stored in the refrigerator overnight and was then stirred for one hour at room temperature and filtered. Five milliliters of methyl alcohol were added and after 10 min. the mixture was refiltered. The filtered mixture was evaporated and 10 ml. of water and 10 ml. of ethyl acetate were added to the residue. The pH of the mixture was adjusted 2, the organic phase separated, and washed with water, dried and evaporated to yield 320 mg. of crude product.

EXAMPLE 8

7-[D-α-(3-Cinnamoyl-3-methyl-1-ureido)-α-phenylacetamido]-3-carbamoyloxymethyl-3-cephem-4-carboxylic acid.

To a suspension of 406 mg. 7-[D-α-amino-α-phenylacetamido]-3-carbamoyloxymethyl-3-cephem-4-carboxylic acid in 8 ml. of acetonitrile containing 2 ml. of propylene oxide was added 1 ml. of BSA. When solution had occurred it was cooled to about −15° C. and a solution of 224 mg. of N-cinnamoyl-N-methylcarbamoyl chloride in 5 ml. of acetonitrile was added with stirring. The mixture was stirred for one hour in the cold and one hour at room temperature and was then poured into a mixture of water:ethyl acetate, 1:1. The pH was adjusted to 8.5 with sodium bicarbonate and the ethyl acetate layer was separated. The aqueous phase was relayered with ethyl acetate and the pH readjusted to pH 2.5 with 1N hydrochloric acid. The ethyl acetate layer was separated, washed with water and brine and dried. Evaporation of the dried solution yielded 170.3 mg. of product.

IR (KBr): 1770 cm$^{-1}$ (β-lactam carbonyl) U.V. (methanol): γ max 278 (ε17,921) Titration 66 percent DMF: pKa 4.98.

I claim:

1. A compound of the formula

[structure: R'''N(H)-C(O)-N(H)-C(O)-N(R")-C(O)-NH-CH(R₁)-C(O)-NH— attached to cephem nucleus with CH₂—O—C(O)—N(H)—R₂ and COOH]

wherein
- R" is hydrogen or methyl;
- R''' is hydrogen, $C_1$–$C_2$ alkyl, allyl, phenyl, benzyl, or furfuryl;
- $R_1$ is 2-thienyl, 2-furyl, phenyl, or phenyl substituted by $C_1$–$C_4$ alkyl, $C_1$–$C_4$ alkoxy, halogen, hydroxy, or nitro;
- $R_2$ is hydrogen or $C_1$–$C_3$ alkyl;

and the pharmaceutically acceptable non-toxic salts thereof.

2. The compound of claim 1 wherein R''' is methyl and $R_2$ is hydrogen or methyl.

3. The compound of claim 1 wherein $R_1$ is phenyl or

[structure: phenyl ring with (Cl)_m and OH substituents]

wherein n is 0, 1, or 2.

4. The compound of claim 3, said compound being 7-[α-(3-methylcarbamoyl-3-methyl-1-ureido)-α-phenylacetamido]-3-carbamoyloxymethyl-3-cephem-4-caboxylic acid.

5. The compound of claim 3, said compound being 7-[α-(3-methylcarbamoyl-3-methyl-1-ureido)-α-phenylacetamido]-3-N-methylcarbamoyloxymethyl-3-cephem-4-carboxylic acid.

6. The compound of claim 3, said compound being 7-[α-(3-methylcarbamoyl-1-ureido)-α-phenylacetamido]-3-carbamoyloxymethyl-3-cephem-4-carboxylic acid.

7. The compound of claim 3, said compound being 7-[D-α-(3-methylcarbamoyl-3-methyl-1-ureido)-α-(4-hydroxyphenyl)acetamido]-3-carbamoyloxymethyl-3-cephem-4-carboxylic acid.

8. The compound of claim 3, said compound being 7-[D-α-(3-methylcarbamoyl-1-ureido)-α-(4-hydroxyphenyl)-acetamido]-3-carbamoyloxymethyl-3-cephem-4-carboxylic acid.

* * * * *